United States Patent [19]

Decker et al.

[11] 4,334,102

[45] Jun. 8, 1982

[54] REMOVING LIQUID HYDROCARBONS FROM POLYETHER SOLVENTS

[75] Inventors: Wilmot H. Decker, Morris Plains; Kurt Theurer, Flanders, both of N.J.

[73] Assignee: Allied Corporation, Morristown, N.J.

[21] Appl. No.: 250,460

[22] Filed: Apr. 2, 1981

[51] Int. Cl.$^3$ .............................................. C07C 41/38
[52] U.S. Cl. .................................. 568/621; 210/634; 55/54; 585/833
[58] Field of Search ...................... 568/621; 210/634; 55/54; 585/833

[56] References Cited

U.S. PATENT DOCUMENTS 3,225,113 12/1965 McNulty et al. .................... 568/621
3,737,392  6/1973 Ameen ................................. 252/364
3,915,674 10/1975 Smith .................................. 568/621

*Primary Examiner*—Howard T. Mars

*Attorney, Agent, or Firm*—Alan M. Doernberg; Gerhard H. Fuchs

[57] ABSTRACT

A method of removing normally liquid hydrocarbons from a polyether solvent such as dimethyl ether of polyethelene glycol by mixing the solution with an aqueous salt solution, removing at a low temperature an organic layer containing liquid hydrocarbons, heating the remaining aqueous layer to a higher temperature where it separates into a second organic layer containing polyether solvent and an aqueous salt solution. The aqueous salt solution is cooled and recycled to mix with additional polyether solvent solution at the low temperature. The process is particularly applicable to removing liquid hydrocarbons which accumulate in recirculating polyether solvents used for absorption of acid gases from feedstocks such as natural gas, synthetic natural gas, ammonia synthesis gas and refinery gas.

15 Claims, 3 Drawing Figures

REMOVING LIQUID HYDROCARBONS FROM POLYETHER SOLVENTS

DESCRIPTION

BACKGROUND OF THE INVENTION

The present invention relates to the removal of liquid hydrocarbons from polyether solvents and especially to the removal of liquid hydrocarbons found in natural gas, synthetic natural gas, synthesis gas and refinery gas which build up in a recirculating polyether solvent when the solvent is used to absorb acid gases from such feedstocks.

A known method of removing acid gases such as hydrogen sulfide, carbon dioxide, COS and methyl mercaptan from the feedstocks is to contact the feed stock at low temperature and high pressure with a polyether solvent such as the dimethyl ether of polyethylene glycol to absorb the acid gases. The liquid is then flashed to remove first absorbed gaseous hydrocarbons and then the bulk of the acid gases. The remaining liquid is called semilean solvent. While some semilean solvent may be recycled to the absorber, some or all of it is generally purified further by stripping with steam or air or other inert gases to remove residual acid gases. In many applications, water present in the semilean solvent can be vaporized by external heating to provide the stripping gas.

Often, however, higher hydrocarbons, and particularly those of 4-8 carbons such as butanes, pentanes, hexanes, heptanes, octanes, benzene, toluene, xylenes and ethylbenzene, are also absorbed in the solvent in increasing amounts in the absorber, even when their concentration in the feedstock gas is relatively low. Because these liquid hydrocarbons are less volatile than methane or other feedstock gases and also less volatile than most acid gases, they will remain predominately in the semilean solvent rather than be flashed off in either step. Lower hydrocarbons such as ethane and propane will also be present to a lesser extent in the semilean solvent. If left in the semilean solvent they can either be stripped in the stripper and/or build up in the solvent returned to the absorber. The former is undesirable if the acid gases are to be used for applications in which hydrocarbon contamination is undesirable, e.g. hydrogen sulfide to be oxidized to sulfur in a Claus plant. The presence of hydrocarbons in hydrogen sulfide fed to a Claus plant causes the resultant sulfur to be brown. Condensing the acid gases to remove the liquid hydrocarbons has the undesirable effect of losing hydrogen sulfide in the condensate, and also requiring energy for both the condensation and subsequent reheating of the acid gases.

Returning the liquid hydrocarbon in the solvent to the absorber has the undesirable effect of increasing the amount of methane, ethane and propane dissolved in the solvent within the absorber and not flashed off. Besides decreasing the fuel value of the purified feed gas, this also results in hydrocarbon contamination of the acid gases recovered in the second and subsequent flashing steps or in stripping steps.

It has been proposed to remove the liquid hydrocarbons especially after cooling, by skimming off the separate layer that forms on the recirculating solvent. Unfortunately, reliance on phase separation alone leaves high levels of liquid hydrocarbons in the solvent. It has been proposed to reduce the residual hydrocarbon content by adding water to the solvent, removing the layer and then removing this water by vaporization. Amounts of water sufficient to appreciably lower hydrocarbon content of the recirculated solvent are so large as to cause an unacceptable amount of energy use for volatilization. Furthermore, unless the water is removed from the solvent, the efficiency of the solvent in absorbing acid gases in the absorber decreases. Thus the need exists for a method of removing liquid hydrocarbons from a polyether solvent without substantially increasing the water content of the solvent.

BRIEF DESCRIPTION OF THE INVENTION

The present invention includes a method of removing normally liquid hydrocarbons from a solution of said normally liquid hydrocarbons in a polyether solvent which is a dialkyl ether of a polyalkylene glycol which comprises:

(a) mixing the solution of normally liquid hydrocarbons in polyether solvent with an aqueous solution of at least 5 weight percent of an inorganic salt relatively insoluble in anhydrous polyether solvent;

(b) removing at a first temperature below about 40° C. a first organic layer containing liquid hydrocarbons from the remaining aqueous layer containing polyether solvent and inorganic salt;

(c) heating the remaining aqueous layer to a second temperature above about 40° C. where the remaining aqueous layer separates into a second organic layer containing polyether solvent and an aqueous salt solution; and (d) removing the aqueous salt solution. The invention is based in part upon the unusual behavior of the liquid system of polyether solvent, water and certain inorganic salts. In preferred forms of the invention, this system in proper ratios forms a single phase at the first temperature, but forms two phases at the second temperature which is higher than the first temperature.

DETAILED DESCRIPTION OF THE INVENTION

Figure 1:
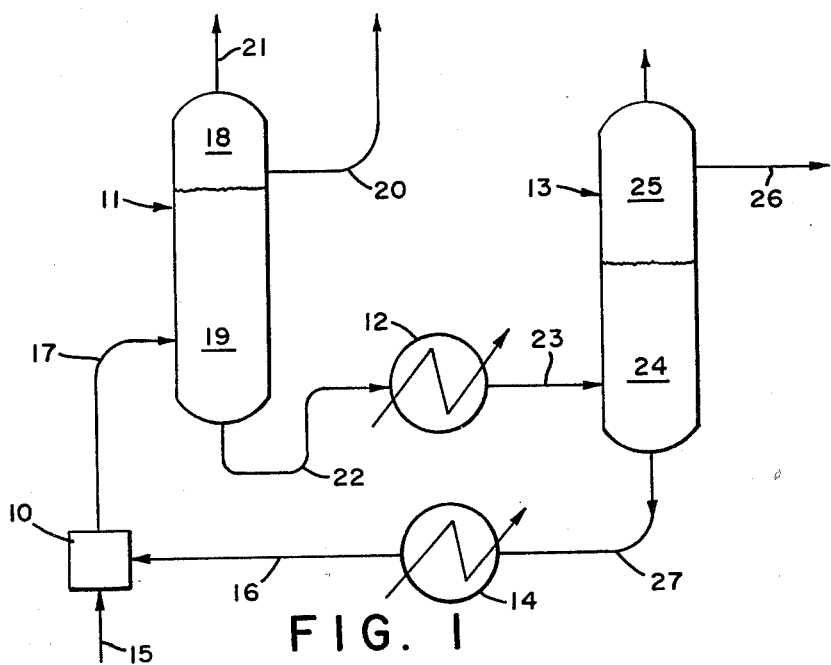

The present invention can be illustrated by reference to the accompanying FIG. 1. In that figure are shown a mixer 10, a settling tank 11, a heating means 12, a second settling tank 13, and a cooling means 14. A stream of polyether solvent containing liquid hydrocarbons, and optionally also containing acid gases such as hydrogen sulfide, carbon dioxide or both is fed in stream 15 to mixer 10. Also fed to mixer 10 is an aqueous salt solution 16 whose concentration, composition and volume proportion to the solvent fed through stream 15 is discussed below. The combined liquids are fed in stream 17 to the first settling tank 11 where, at the low temperature (hereinafter called the first temperature) prevalent in streams 15, 16 and 17, the liquid separates into a small organic phase 18 and a large aqueous phase 19. The organic phase 18 contains predominately liquid hydrocarbons such as butane, hexane, benzene, toluene, xylenes, and the like, depending upon which hydrocarbons were initially present in stream 15. Such liquid hydrocarbons are withdrawn periodically from settling tank 11 through stream 20. In addition, if somewhat more volatile hydrocarbons such as butane were present in stream 15, they will also be present in organic layer 18 and, sometimes, can be conveniently vented through vent 21 at the top of settling tank 11. The presence of vent 21 also operates as a safety feature.

The aqueous phase 19 is withdrawn from the bottom of settling tank 11 through stream 22, heated in heating means 12 such as heat exchanger to a temperature (hereinafter called the second temperature) above about 40° C., preferably above about 50° C. and suitably up to a temperature where significant vapor pressure develops. The heated stream 23 is fed to a second settling tank 13 where it separates to an aqueous layer 24 and an organic layer 25. The organic layer 25 now contains a polyether solvent, relatively little liquid hydrocarbons, some water, relatively minor amounts of salt and essentially all of the acid gases fed into mixer 10 through stream 15. This organic layer of purified solvent is withdrawn through stream 26. The aqueous layer 24 contains water and salt predominately, some solvent, and essentially no liquid hydrocarbons or acid gases. It is withdrawn through the bottom of the second settling tank 13 through stream 27, cooled by cooling means 14 back to a temperature below 40° C., and preferably below 25° C., desirable for the operation of the first settling tank 11 and then fed through stream 16 to mixer 10.

Figure 2:
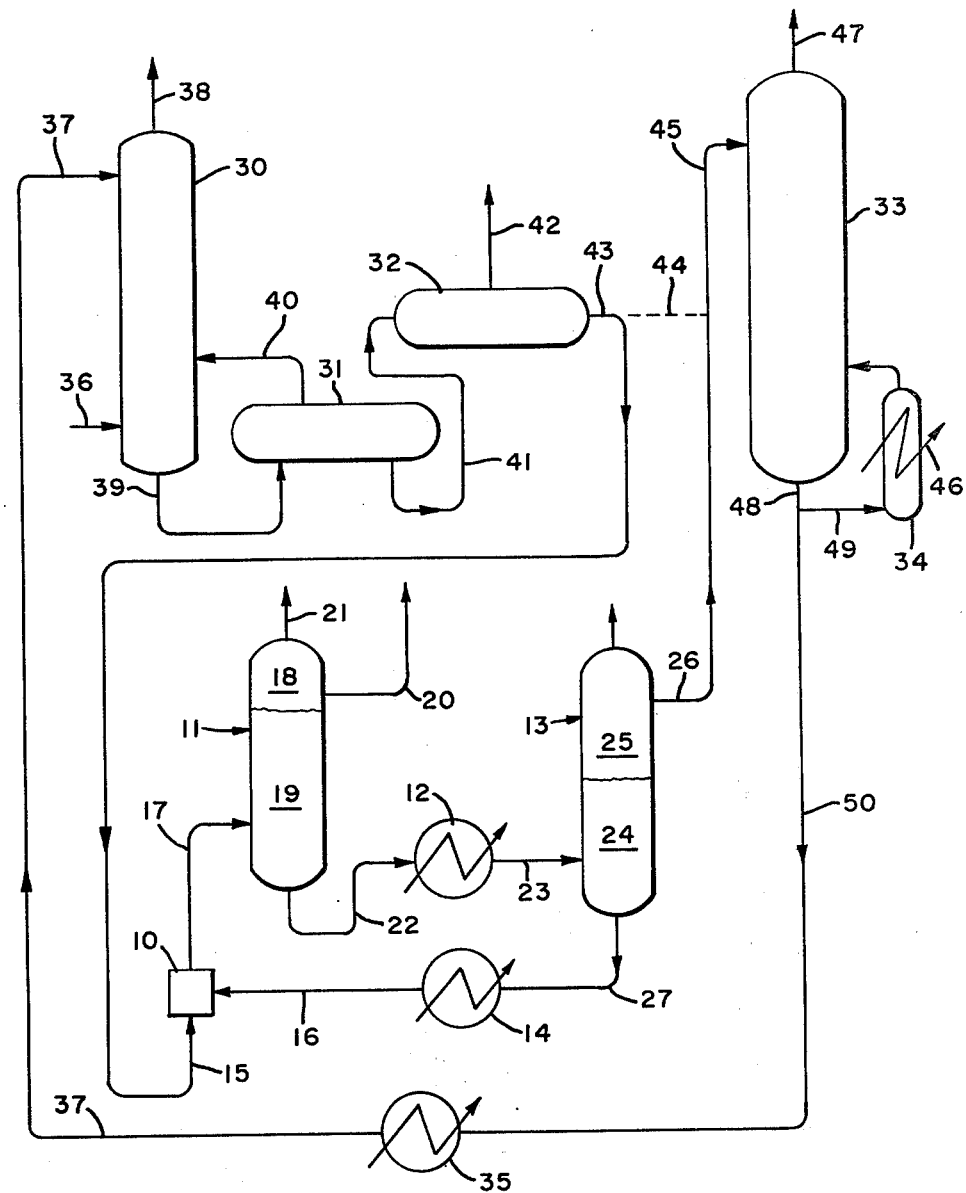

FIG. 2 illustrates the process of the present invention practiced in conjunction with an absorption system using a polyether solvent to remove hydrogen sulfide from a sour feedstock gas such as natural gas. Elements 10–26 performs substantially as described above in relation to FIG. 1. The conventional apparatus portions of the absorption system are absorber 30, first flash tank 31, second flash tank 32, stripping column 33, reboiler 34, and cooling means 35.

The operation of the system of FIG. 2 is as follows. The natural gas feedstock is fed to absorbing column 30 near its base in stream 36. A polyether solvent is fed near the top of the absorbing column 30 in stream 37. By conventional countercurrent absorption, acid gases are absorbed from the feedstock gas into the polyether solvent such that, by the time the polyether solvent is withdrawn from the base of the absorbing column 30 in stream 39, it contains substantially all of the acid gases present in the natural gas. Thus, the natural gas leaving the absorbing column 30 at the top through stream 38 is "sweet" or free of hydrogen sulfide and, depending upon operating conditions, other acid gases. Absorber 30 operates at relatively high pressures and relatively low temperatures such as greater than about 10 atmospheres (preferably above about 50 atmospheres) pressure and less than about 55° C. (preferably less than about 20° C.).

The liquid in stream 39 is reduced somewhat in pressure and then flashed in flash tank 31. The gas flashed off, principally methane and other volatile hydrocarbons such as ethane and propane, is returned in stream 40 to the absorbing column 30, usually after both recompression and cooling. The remaining liquid is removed from flash tank 31 in stream 41, expanded to a still lower pressure and then flashed in the second flash tank 32. The gases flashed off are removed in stream 42 and consist principally of acid gases such as hydrogen sulfide. The liquid may be flashed again in one or more subsequent flashing steps at increasingly lower pressures but, for simplicity sake, it is assumed that only two flash vessels 31 and 32 are employed. The liquid now in stream 43 would be conducted in a conventional system through stream 44 to stream 45 where it would be fed to stripping column 33. In practice of the present invention, however, the liquid in stream 43 is diverted to stream 15 and fed into mixing tank 10. The result of the passage of the solvent, called semilean solvent, through mixer 10, first settling tank 11, heating means 12 and second settling tank 13 is that liquid hydrocarbons which have been absorbed from the feed gas in stream 36 into the polyether solvent in the absorber 30 are now removed from the polyether solvent. Depending upon the amount of water present in the polyether solvent when fed to the absorbing column 30 in stream 37, it may now have increased its water content between stream 15 and stream 26. Additionally, very minor amounts of salt may have dissolved in the polyether solvent. If this amount of water is appreciable, some make up water may be required to be combined into stream 27 or stream 16 so as not to increase the salt concentration to the point where crystallization occurs.

Stream 26 is then fed to stream 45 which is fed into the stripping column 33 near the top. The liquid, being hot but not hot enough for water to vaporize immediately, falls down within stripping vessel 33 and contacts upcoming hot gases which are principally steam. This steam exists the stripping column 33 through stream 47 as hot steam containing the residual acid gases which were present in stream 45. A portion of the liquid in stream 48 is fed to a reboiler 34 where it is heated, e.g. by passage in heat exchange with steam 46 and returned to the stripping column 33. Thus reboiler 34 provides the heat to vaporize water from the polyether solvent containing water which is fed into the stripping column in stream 45. If more water is present in the polyether solvent in stream 26 than was present in the polyether solvent in 43, than it may be desirable to increase the heat input into reboiler 34 sufficiently to reduce the water content of stream 48 to the same level as if the polyether solvent in stream 43 were fed through streams 44 and 45 to the stripping column 33. The hot polyether solvent, now stripped of liquid hydrocarbons, acid gases and much of its water content is returned through stream 50, cooling means 35 and stream 37 to the absorbing column 30.

The above description is intended to illustrate the role of the present process in a recirculating polyether solvent gas purification system. In general, the result of its use is to remove liquid hydrocarbons from the system through stream 20 so that they do not build up in the recirculating solvent fed in stream 37 back to the absorbing column 30. If liquid hydrocarbons remained in the polyether solvent in increasing amounts, first the acid gases in stream 47 and then the acid gases in stream 42 would be contaminated with increasing amounts of volatilized liquid hydrocarbons until a steady state concentration was reached. Furthermore, an increasing proportion of lower hydrocarbons, and especially ethane and propane, but also methane, would be dissolved by the liquid hydrocarbons into the liquid phase and be withdrawn from the absorbing column 30 in stream 39. If this increasing amount of lower hydrocarbons in the liquid were not completely flashed into stream 40, it would also flash in the second flash vessel 32 and contaminate the acid gases in stream 42. By comparison to the use of water alone to expell the liquid hydrocarbons from the polyether solvent, less water is introduced into the polyether solvent and, therefore, the energy load required to operate stripping column 33 is not increased as much.

It is contemplated that various energy conservation techniques can be used in the practice of the present invention in conjunction with the gas purification system. Thus, for example, the heating of combined polyether solvent and aqueous salt accomplished in heating means 12 can be combined with the cooling of aqueous salt solution in cooling means 14 and the cooling of polyether solvent in cooling means 35 by the use of suitable heat exchangers. Thus the liquid in stream 22 may first be heated by heat exchange with the liquid in stream 27, then by heat exchange with the liquid in stream 50 and finally if necessary to achieve the desired high temperature, by heat exchange with steam. The liquid in stream 27 may be cooled first by heat exchange with the liquid in stream 22 and then, only if necessary, by heat exchange with cooling water or refrigeration. The liquid in stream 50 may be cooled first by heat exchange with the partially cooled liquid in stream 22, then by heat exchange with cooling water and only then by refrigeration. Other suitable energy conservation techniques will be apparent to one skilled in the art.

It should be appreciated that, in conventional operations where the liquid in stream 43 is fed through streams 44 and 45 to the stripping column 33, it is usually preheated to near the temperature desired for operation in stripping column 33 by heat exchange with the liquid leaving stripping column 50. Thus stream 44 usually includes a portion through heat exchanger 35 in heat exchange relation to the liquid in stream 50. When using the present invention, and particularly heating means 12, the same heating function can be accomplished in essentially the same way. The only additional load, therefore, is that aqueous salt as well as solvent must be heated and, conversely, the aqueous salt must be cooled back down in cooling means 14. With proper use of heat exchangers, relatively little external heating or external cooling is required.

Figure 3:
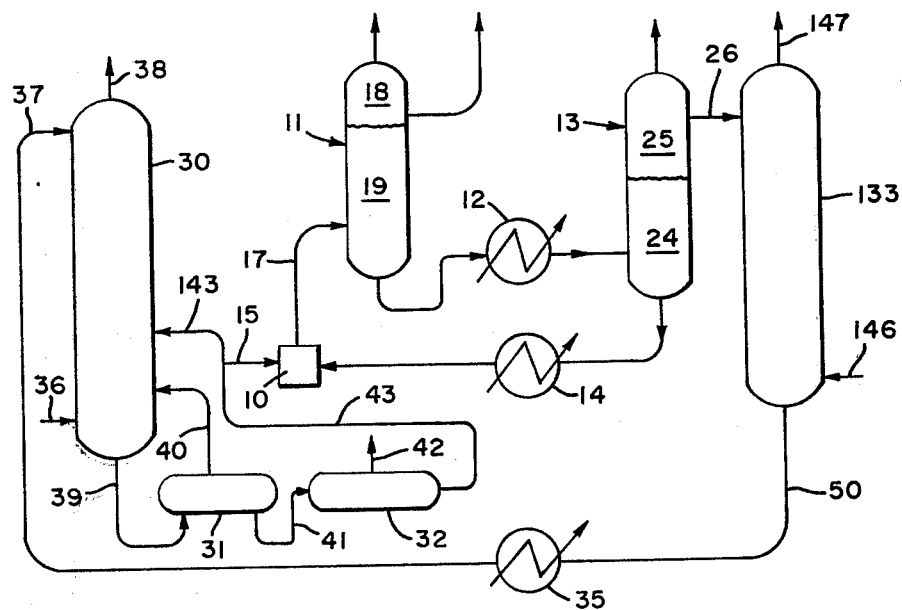

FIG. 3 illustrates the use of the present process in a gas purification scheme employing a recirculating polyether solvent of a slightly different configuration. In general, the operation illustrated in FIG. 3 is more applicable to gases from which it is desired to remove carbon dioxide rather than gases from which it is desired to remove hydrogen sulfide. The feed gases are fed in stream 36 to base of absorber 30 and removed through stream 38 from the top of the absorbing column 30. Recirculated polyether solvent is fed in stream 37 near the top of absorbing column 30 and removed from the base of the column 30 through stream 39. Acid gases, and particularly carbon dioxide, are removed from the gas such that stream 38 is relatively low in carbon dioxide, and liquid stream 39 contains substantial amounts of carbon dioxide. The liquid stream is flashed in first flashed tank 31 and the flashed gases recompressed, cooled and returned in stream 40 to the absorbing column 30. The liquid is then reduced further in pressure and flashed in flash tank 32 to remove flashed gases 42, consisting principally of acid gases. The remaining liquid in stream 43 is then partitioned into a first portion 143 which is recompressed and fed to an intermediate point in absorbing column 30. This semilean solvent is effective to remove acid gases from the gas phase in the column, but not to lower the acid gas content to the level desired for stream 38. Accordingly, it is only the leaner solvent in stream 37 which contacts the gas near the top of the column. The remainder of the semilean liquid is fed in stream 15 to mixer 10 and then extracted at low and high temperatures as described above in relation to FIG. 1. The second organic phase 25 contains substantially less liquid hydrocarbons, some additional water and a relatively minor amount of salt compared to the semilean solvent fed in stream 15. This second organic phase 25 is fed in stream 26 to a point near the top of a stripping column 133. An inert gas is fed in stream 146 near the base of stripping column 133, which therefore operates at whatever temperature the liquid in stream 26 is. The inert gas strips the residual acid gases from the second organic layer and removes them in stream 147 at the top of stripping column 133. The liquid is removed from the base of the stripping column 133 in stream 50 and fed through cooling means 35 back to stream 37 and the top of the absorbing column 30.

Like the operations described in relation to FIG. 2, the process described in FIG. 3 reduces the liquid hydrocarbon content of the recirculated polyether solvent. Since, however, the stripping column works without volatilization of water, it is generally desirable in the operation of the process described in FIG. 3 to limit the high temperature in the second settling tank 13 to as low as temperature as possible so as to decrease the load upon cooling means 35. While heat exchange is still possible to accomplish the heating required for heating means 12 and the cooling required for cooling means 14 and 35, some external heat must generally be required to be applied in heating means 12, and some cooling water or refrigeration will generally be required in both cooling means 14 and cooling means 35. It should be appreciated, however, that some heating or cooling may be available by heat exchange with compressed and/or expanded fluids in streams adjacent flash tanks 31 and 32. It is also important in the system described in FIG. 3 to increase the water content of the solvent as little as possible during passage through mixer 10, first settling tank 11 in second settling tank 15 so as to prevent water build up in the system. Depending upon temperature at which stripping column 133 operates, some water may be swept from the system and removed through stream 147.

While, in general, the choice of a particular salt, its concentration in the aqueous solution, the ratio of aqueous solution to polyether solvent mixed and the particular first and second temperatures are not critical, it is necessary to interrelate them based upon the following criteria. First, the salt must be dissolved in the aqueous solution at the low temperature at the desired concentration, which is at least about 5 weight percent, preferably at least about 10 percent and more preferably as high as possible consistent with the other criteria. Many inorganic salts which have only limited solubilities in water are unsuitable based on this criteria. Second, the salt must be relatively insoluble in the polyether solvent at the higher temperature. A representative criteria for preferred salt is one that is soluble to an extent less than 0.01 percent in anhydrous polyether and less than 0.1 percent in polyether containing 5 percent water. The third criterion is that the salt should not crystallize at the low temperature when the aqueous solution and polyether solvent are mixed. This criterion operates as a limitation on a selection of salts, the permitted salt concentration in the aqueous solution and on the mixing ratio between aqueous solution and polyether solvent. The fourth criterion is that the salt should remain in the liquid phase, and not crystallize out, at the high temperature in the aqueous phase which separates from the second organic layer. Since most salts are more soluble in water at higher temperatures than at lower temperatures, this criterion is generally met when the first criterion is met. Because, however, some water is removed from the aqueous layer by the treatment and, because some salts are less soluble at higher temperatures, this fourth criterion may place some additional limitations upon the selection of salt, concentration of salt in the initial aqueous solution and mixing ratio.

It is preferred, but not required, that the aqueous solution and the polyether be miscible in the mixing proportions at the lower temperature. This permits the aqueous phase shown as element 19 in all three figures to be a single phase, rather than a polyether phase containing dissolved water and a water phase containing dissolved polyether. It should be appreciated that the desired effect is to have salt present in the polyether phase so as to expel liquid hydrocarbons from this phase. Since, based upon the first two criteria, the salt would be present in much higher concentrations in the water phase than in a polyether phase, the presence of these two separate phases is likely to defeat the purpose of the invention. Nevertheless, it may be possible with certain salts which are highly soluble in water that sufficient salt concentrations will still be present in the polyether rich phase of a three phase system at low temperature to expel liquid hydrocarbons.

The salt should also be chosen, in combination with various operating conditions and materials of construction, to minimize corrosion. Thus, for example by reference to FIG. 2, vessels and heat exchangers 11, 12, 13 and 14 should be of materials resistant to corrosion by the fluids contained therein which contain substantial salt concentrations. It should be appreciated that corrosion is less of a problem with basic salts like sodium formate than with acidic salts such as ammonium sulfate. Furthermore, the salt, at its low concentration in phase 25 should be compatible with, and not corrode substantially, vessels 33, 34 and 35 at the relatively high temperatures present therein. In general, if corrosion in vessels 33, 34 and 35 is minimal, corrosion in vessels 30, 31 and 32 will be most unlikely, since the temperatures therein are substantially lower. Nevertheless, some care might be required in choosing a packing or tray material for absorber 30 that is not corroded by the solvent which contains the low salt level.

Preferred salts include alkali metal halides, formates and acetates, especially where the alkali metal is Na or K and the halide is Cl. Especially preferred are potassium formate and acetate. Preferably the aqueous salt solution contains at least 10 weight percent inorganic salt.

The present invention is applicable to polyether solvents generally, but is particularly applicable to diethyl ethers of polyalkylene glycols with alkyl of 1-5 carbons (especially methyl) and alkylene of 2-6 carbons (especially ethylene). A preferred group of polyether solvents are mixtures of polyethers of the formula

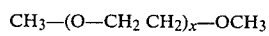

$$CH_3-(O-CH_2\,CH_2)_x-OCH_3$$

wherein x is between 3 and 8 for at least 95 mol percent of the mixture. U.S. Pat. No. 3,737,392 describes some such mixtures.

The first and second temperature will depend upon the chosen salt and salt concentration, with suitable temperatures easily determined as in Example 1, below. Preferably, the first temperatue is below about 25° C. (but above any crystallization temperature) and the second temperature is above about 50° C. (but below any boiling temperature). Preferred mixing ratios of polyether solvent to aqueous salt solution are between about 5:1 and about 1:5.

In most embodiments of the invention, the aqueous salt solution removed in step c at the second temperature is cooled to a third temperature not substantially higher than the first temperature and recycled to the mixing step. If the polyether to be regenerated contains a minor proportion of hydrogen sulfide as one of the acid gases, as well as normally liquid hydrocarbons, the minor proportion of hydrogen sulfide will be present in the second organic layer. In such cases, the acid gases, and especially hydrogen sulfide, are stripped from the second organic layer by contact with a gas stream such as steam. The steam preferably includes steam generated by heating the second organic layer to 100° C. to volatilize water in the second organic layer. Additional live steam may also be introduced. As indicated above in the description of FIG. 2, the heating from the first temperature to the second temperature would be required in any event if the solvent were to be stripped of water by steam stripping. While the present process does increase somewhat the water content of the organic layer going into the steam stripper, it is believed not to impose a major energy penalty on the total operation of the system.

EXAMPLE 1 - Screening of Salts

A series of salts were screened for low solubility at 21° C. in dimethyl ether of polyethylene glycol of a homolog mixture as described in U.S. Pat. No. 3,737,392 and having under 5% water. Only NaI, NaBr, NH$_4$Br, NaSCN and KSCN among the single salts showed substantial (greater than 0.5%) solubility in the solvent. Salts which had limits of 0.1 or 0.2 mL saturated aqueous solution in 50 mL solvent included potassium formate, potassium acetate, sodium chloride, ammonium chloride, potassium chlorate, ammonium sulfate and monosodium phosphate. Other salts soluble to the extent of less than 0.5% included KHSO$_4$ and KH$_2$PO$_4$. Sodium benzoate and sodium methane sulfonate were insoluble in dry solvent, but had limited solubility as the water content of the solvent increased to 4%. Disodium adipate had minimal solubility in dry solvent and solvent with up to 4% water. Sodium toluene sulfonate was soluble at less than 0.1% in dry solvent and less than 0.2% in solvent with 2% water.

It should be appreciated that the solubility of a given salt in a given polyether solvent at a given temperature can be determined by routine experimentation.

EXAMPLE 2

80 mL of the solvent of Example 1 containing 5% water by weight were mixed with 20 mL of each of the aqueous solutions indicated in Table 1. The number of phases was observed at room temperature. If one phase existed at room temperature, the solution was heated until two phases formed or 100° C. was reached. If two phases formed, the volume of the lower phase at 90° C. was measured. If the lower phase at 90° C. contained at least 15 mL, salt concentration was considered sufficiently high.

TABLE 1

| Aqueous Solution | Conc.* | Two Phases Form At About | Lower Phase At 90° C. |
|---|---|---|---|
| KCOOH | 15 | 65° C. | 7 mL |
| KCOOH | 25 | 50° C. | 12 mL |
| KCOOH | 35 | 35° C. | 15 mL |
| KCOOH | 50 | 25° C. | 18 mL |
| KC$_2$H$_3$O$_2$ | 25 | 55° C. | 14 mL |
| KC$_2$H$_3$O$_2$ | 40 | 37° C. | 15 mL |
| NaCOOH | 21 | 21° C. | 12 mL |

TABLE 1-continued

| Aqueous Solution | Conc.* | Two Phases Form At About | Lower Phase At 90° C. |
|---|---|---|---|
| NaCOOH | 25 | 21° C. | 15 mL |
| NaC$_2$H$_3$O$_2$ | 25 | 21° C. | 14 mL |
| NaC$_2$H$_3$O$_2$ | 40 | 21° C. | 17 mL |
| NaCl | 25 | 55° C. | 15 mL |
| NaI | 25 | One Phase at 100° C. | — |
| KCl | 25 | 25° C. | 10 mL |
| Na$_2$SO$_4$ | 25 | 25° C.** | 5–10 mL |

*as g/100 ml solution
**insoluble salts present at 25° C., semisolid materials present at 90° C. on walls of vessel.

It should be appreciated that, for a given solvent, salts can be screened in like manner for system which are one-phase at low temperatures, two-phase at higher temperatures and return most of the aqueous phase at a higher temperature such as 90° C.

EXAMPLE 3

A sample of polyether solvent from a gas purification system which had about 9% dissolved oils and 0.3% water was mixed with equal volumes of 10% NaCl in water. An oil layer about 8.4% of the volume of the solvent formed. This is a standard test for oil content in such solvents.

40 volume parts of such solvent were mixed with 10, 20 and 30 volume parts of aqueous NaCl (25 g/100 mL). With 10 parts salt solution, the phases remained separate at room temperature. With 20 parts aqueous salt, more oil layering was observed. With 30 parts aqueous salt one large phase and about 3.5 volume parts oil were observed. This represents about 8.8% of the original solvent by volume. This oil layer was removed and the remaining layer heated to about 90° C. Two phases formed as the temperature was raised, with the lower aqueous phase containing at 90° C. about 29 volume parts, or over 95% of the original aqueous salt solution.

EXAMPLE 4

50 mL synthetic mixture containing 3.9 wt. % water, 6.0 wt. % n-heptane (equivalent to 8.8 vol. %) and 90.1 wt. % polyether was mixed with 50 mL of 30 weight % aqueous potassium formate at room temperature. Two layers formed. The upper hydrocarbon layer, approximately 4 mL in volume and equivalent to approximately 90% recovery, was found to contain 3% polyether and 0.2% potassium formate, by weight. The lower aqueous salt/polyether layer was heated to 90° C. Two phases formed as the temperature was raised. The upper polyether phase contained <1 vol. % n-heptane, 15.3% water and 1.0% potassium formate. The lower aqueous salt phase contained approximately 10 weight % polyether.

EXAMPLE 5

50 mL synthetic mixture containing 3.9 wt. % water, 6.0 wt. % n-heptane (equivalent to 8.8 vol %) and 90.1 wt. % polyether was mixed with 60 mL of 37 weight % aqueous potassium acetate at room temperature. Two layers formed. The upper hydrocarbon layer, approximately 4 mL in volume and equivalent to approximately 90% recovery, was found to contain 5% polyether and 0.1% potassium acetate, by weight. The lower aqueous salt/polyether layer was heated to 90° C. Two phases formed as the temperature was raised. The upper polyether phase contained <1 vol. % n-heptane, 9.2% water and 0.62% potassium acetate, by weight. The lower aqueous salt phase contained approximately 11 weight % polyether.

EXAMPLE 6

A sample of polyether solvent from a gas purification system which had about 5 volume percent dissolved hydrocarbon oils and 4.8 weight percent water was mixed at room temperature with three volumes of 37 weight percent potassium formate in water. Two layers formed. The upper hydrocarbon layer, approximately equivalent to 5 volume percent dissolved hydrocarbon oils was removed. The lower aqueous salt/polyether layer was heated to 90° C. Two phases formed as the temperature was raised. The upper polyether phase was separated from the lower aqueous salt phase by decantation. The lower aqueous salt phase was cooled to room temperature and the above described procedure repeated two additional times with fresh polyether solvent from the gas purification system. The recycled aqueous salt solution after contacting fresh polyether solvent for three times contained approximately 4 weight percent polyether. The polyether solvent recovered from the third extraction contained 8.3 weight percent water, 0.48 weight percent potassium formate and less than 0.5 volume percent dissolved hydrocarbon oils.

EXAMPLE 7

A sample of polyether solvent from a gas purification system which had about 5 volume percent dissolved hydrocarbon oils and 4.8 weight percent water was mixed at room temperature with three volumes of 43 weight percent potassium acetate in water. Two layers formed. The upper hydrocarbon layer, approximately equivalent to 5 volume percent dissolved hydrocarbon oils was removed. The lower aqueous salt/polyether layer was heated to 90° C. Two phases formed as the temperature was raised. The upper polyether phase was separated from the lower aqueous salt phase by decantation. The lower aqueous salt phase was cooled to room temperature and the above described procedure repeated two additional times with fresh polyether solvent from the gas purification system. The recycled aqueous salt solution after contacting fresh polyether solvent for three times contained approximately 5 weight percent polyether. The polyether solvent recovered from the third extraction test contained 6.4 weight percent water, 0.61 weight percent potassium acetate and approximately 0.5 volume percent dissolved hydrocarbon oils. Hydrocarbon recovery was slightly lower than observed in example 6. The reason is that the higher salt concentration used in Example 7 increased the coalescence time for the hydrocarbon phase.

What is claimed is:

1. A method of removing normally liquid hydrocarbons from a solution of said normally liquid hydrocarbons in a polyether solvent which is a dialkyl ether of a polyalkylene glycol which comprises:
    (a) mixing the solution of normally liquid hydrocarbons in polyether solvent with an aqueous solution of at least 5 weight percent of a salt relatively insoluble in anhydrous polyether solvent;
    (b) removing at a first temperature below about 40° C. a first organic layer containing liquid hydrocarbons from the remaining aqueous layer containing polyether solvent and salt;
    (c) heating the remaining aqueous layer to a second temperature above about 40° C. where the remaining aqueous layer separates into a second organic layer containing polyether solvent and an aqueous salt solution; and (d) removing the aqueous salt solution.

2. The method of claim 1 wherein the aqueous salt solution removed from the second organic layer is cooled to a third temperature not substantially higher than the first temperature and recycled to said mixing step.

3. The method of claim 1 wherein the polyether solvent is a dialkyl ether of a polyalkylene glycol with alkyl of 1–5 carbons and alkylene of 2–6 carbons.

4. The method of claim 3 wherein alkyl is methyl.

5. The method of claim 4 wherein alkylene is ethylene.

6. The method of claim 5 wherein the polyether solvent is a mixture of ethers of the formula $$CH_3-(O-CH_2CH_2)_xOCH_3$$

wherein x is between 3 and 8 for at least about 95 mol percent of the mixture.

7. The method of claim 1 or 5 or 6 wherein the salt is an alkali metal halide, formate or acetate.

8. The method of claim 7 wherein the salt is potassium formate.

9. The method of claim 7 wherein the salt is potassium acetate.

10. The method of claim 1 wherein the aqueous salt solution contains at least 10 weight percent salt.

11. The method of claim 1 or 10 wherein the first temperature is below about 25° C. and the second temperature is above about 50° C.

12. The method of claim 1 wherein the solution of normally liquid hydrocarbon in polyether solvent is mixed with the aqueous salt solution at a volume ratio between about 5:1 and about 1:5.

13. The method of claim 1 wherein the solution of normally liquid hydrocarbons in polyether solvent further contains a minor proportion of hydrogen sulfide, the minor proportion of hydrogen sulfide is present in the second organic layer and the second organic layer is contacted with a gas stream to strip the minor portion of hydrogen sulfide.

14. The method of claim 13 wherein steam is volatilized from the second organic layer and such steam is the gas stream used to strip the minor proportion of hydrogen sulfide.

15. The method of claim 1 wherein the normally liquid hydrocarbons contain predominately aromatic and aliphatic hydrocarbons of 4–8 carbons.

* * * * *